U S012307556B2

United States Patent
Veronesi et al.

(10) Patent No.: US 12,307,556 B2
(45) Date of Patent: May 20, 2025

(54) AUTOMATIC MODEL-BASED NAVIGATION SYSTEM AND METHOD FOR ULTRASOUND IMAGES

(71) Applicant: GE Precision Healthcare LLC, Wauwatosa, WI (US)

(72) Inventors: Federico Veronesi, Bologna (IT); Olivier Gerard, Oslo (NO)

(73) Assignee: GE Precision Healthcare LLC, Wauwatosa, WI (US)

( * ) Notice: Subject to any disclaimer, the term of this patent is extended or adjusted under 35 U.S.C. 154(b) by 598 days.

(21) Appl. No.: 17/208,505

(22) Filed: Mar. 22, 2021

(65) Prior Publication Data
US 2022/0301240 A1    Sep. 22, 2022

(51) Int. Cl.
G06T 11/00    (2006.01)
A61B 8/00    (2006.01)
A61B 8/14    (2006.01)
G06T 7/38    (2017.01)
G06T 17/00    (2006.01)

(52) U.S. Cl.
CPC .......... *G06T 11/003* (2013.01); *A61B 8/4245* (2013.01); *A61B 8/463* (2013.01); *A61B 8/466* (2013.01); *A61B 8/483* (2013.01); *G06T 7/38* (2017.01); *G06T 17/00* (2013.01);
(Continued)

(58) Field of Classification Search
CPC ......... G06T 11/003; G06T 7/38; G06T 17/00; G06T 2207/10132; G06T 2207/30048; A61B 8/4245; A61B 8/463; A61B 8/466; A61B 8/483
See application file for complete search history.

(56) References Cited

U.S. PATENT DOCUMENTS 8,265,363 B2 *  9/2012  Orderud ................ A61B 8/483
                                                382/160
2015/0302638 A1 * 10/2015  Jago .......................... G06T 7/30
                                                345/420
(Continued)

OTHER PUBLICATIONS

J. Hansegard et al., "Real-time active shape models for segmentation of 3D cardiac ultrasound", Computer Analysis of Images and Patterns, Berlin, Germany, Spring, 2007, vol. 4673, LNCS, pp. 157-164.

*Primary Examiner* — Matthew C Bella
*Assistant Examiner* — Janice E. Vaz
(74) *Attorney, Agent, or Firm* — Boyle Frederickson S.C (57) ABSTRACT

The system and method employ anatomical information provided via a detailed anatomical 3D model to generate 2D view bookmarks or short-cuts defined with reward to the 3D model. These short-cuts utilize the information provided by the 3D model to determine the optimal positions for acquisition of 2D images of particular desired views or structures based on the structure of the 3D anatomical model. Because the short-cuts are based on the structure of the 3D model, when the model is registered to a 3D volume generated from the 3D echocardiographic dataset for any patient, the short-cuts are directly applicable to obtaining 3D/2D images generated from the 3D dataset. In addition, the 3D model assists the user with regard to the navigation of the 3D dataset using the 3D volume and/or 2D planar views by providing known anatomical reference(s) in the 3D model correlating to the reference(s) in the displayed views.

15 Claims, 8 Drawing Sheets

(52) U.S. Cl.
CPC ....... *A61B 8/14* (2013.01); *G06T 2207/10132* (2013.01); *G06T 2207/30048* (2013.01)

(56) References Cited

U.S. PATENT DOCUMENTS

| | | | |
|---|---|---|---|
| 2016/0038121 A1* | 2/2016 | Waechter-Stehle | A61B 8/14 600/443 |
| 2016/0249885 A1* | 9/2016 | Schneider | G01S 7/52074 382/131 |
| 2017/0119355 A1* | 5/2017 | Pintoffl | A61B 8/54 |
| 2017/0238907 A1* | 8/2017 | Kommu Chs | A61B 8/5223 |
| 2017/0360402 A1* | 12/2017 | de Jonge | G06V 10/454 |
| 2018/0344290 A1* | 12/2018 | Veronesi | A61B 8/466 |
| 2018/0350064 A1* | 12/2018 | Man | A61B 8/483 |
| 2020/0237347 A1* | 7/2020 | De Beni | A61B 8/5261 |

\* cited by examiner

AUTOMATIC MODEL-BASED NAVIGATION SYSTEM AND METHOD FOR ULTRASOUND IMAGES

BACKGROUND OF THE INVENTION

Embodiments of the subject matter disclosed herein relate to medical imaging, and more particularly, to the display of ultrasound imaging devices to a practitioner.

An ultrasound imaging system typically includes an ultrasound probe that is applied to a patient's body and a workstation or device that is operably coupled to the probe. The probe may be controlled by an operator of the system and is configured to transmit and receive ultrasound signals/image data that are processed into an ultrasound image by the workstation or device. The workstation or device may show or display the ultrasound images through a display device. For the display of the ultrasound images, the image data/dataset obtained by the probe is utilized by the ultrasound imaging system to generate multiple images of the structure being imaged by the probe.

In one example of these types of images, the image data/dataset is a three dimensional (3D) image dataset that can be rendered into a 3D volume that is utilized to generate images of multiple planes of the imaged structure that are presented to the user of the ultrasound imaging system. The process for producing these planar images involves multiplanar reconstruction (MPR) and allows effective display of 3D image dataset by providing multiple planes, which are typically three (3) orthogonal 2D planes, in association with the 3D volume. The 3D volume 1000 is sliced at different locations and with different orientation to form the 2D planar views or images 1002 that are presented with the 3D volume 1000 in the MPR display 1004, as shown in FIG. 1.

Figure 1:
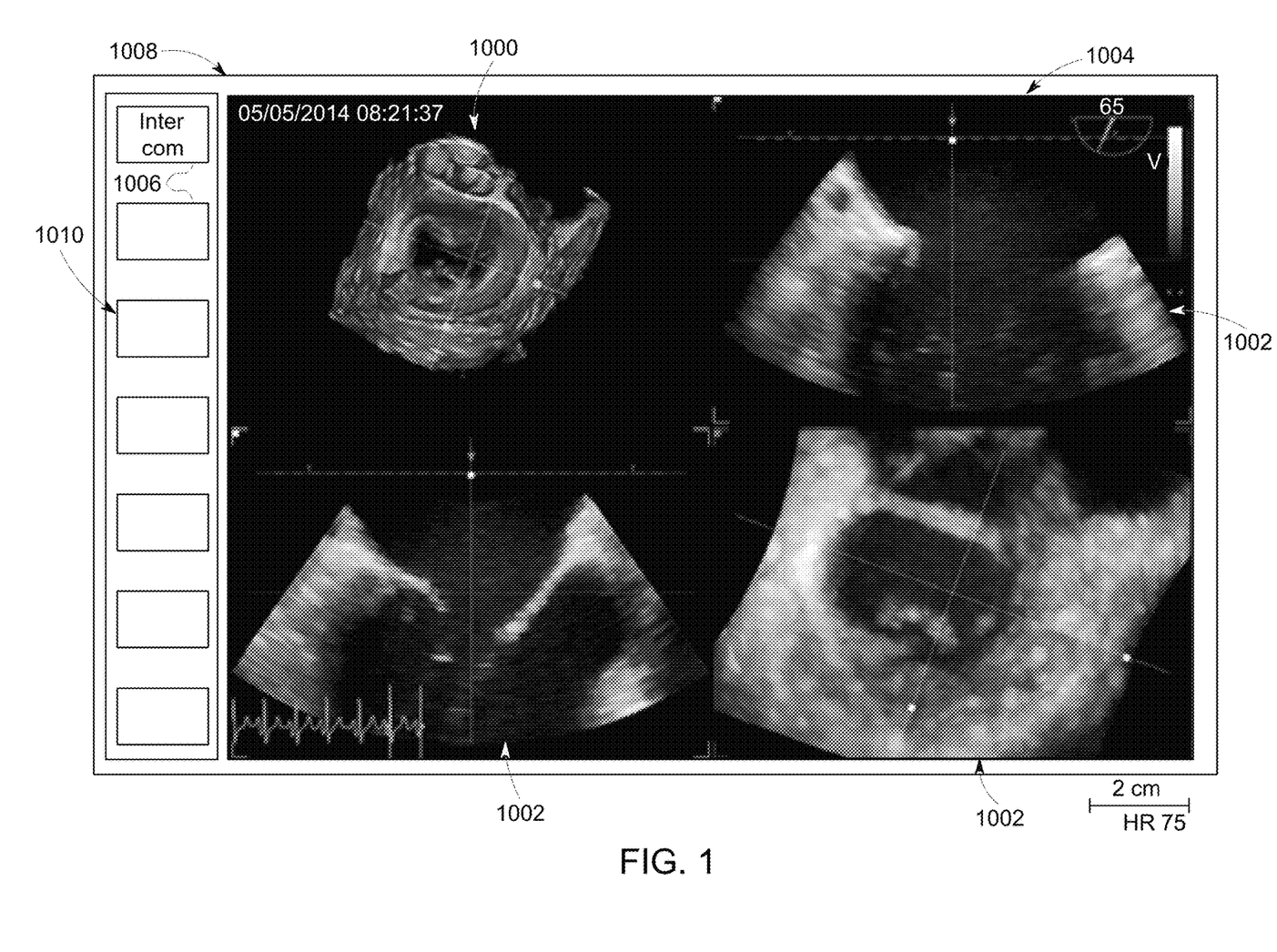
FIG. 1 is an illustration of a prior art display for a multi-planar reconstruction views for an ultrasound imaging system.

To enhance the speed for obtaining desired views of the patient anatomy, certain ultrasound imaging systems provide short-cuts 1006 on a display 1008 for the system that relate to particular standard views to be obtained of the patient, as show in FIG. 1. The short-cuts 1006 provide in the user with acquisition parameters, including the mode of acquisition of the image dataset, e.g., 2D, 3D, and/or 4D, without or with color flow (CF), depth, width, angles of planes, etc., and with display parameters, including the layout on screen, orientation of 3D data, position of crop plane, etc., in order to achieve the selected image associated with the short-cut 1006. This feature allows a user to quickly select a desired view from a menu or list 1010 of short-cuts 1006 presented on the user interface display screen 1008 for the system, and having the system present the required probe position and angle for that view.

One limitation of these types of systems and methods is that all stored parameters for the provided short-cuts 1006 are linked to a standardized probe position for the associated view and not to the anatomical structure of interest in the patient. For instance, when selecting an "Inter-Com" short-cut 1006 on the screen 1008, which stands for Inter-Commissure view for the mitral valve, the system sets an acquisition with a probe angle at 60°, which is the "standard" or average among all patients. However, the current patient may have an anatomical structure for which this average or standard angle/setting is not optimal. As a result, the user will have to manipulate the probe to reach the correct angle to provide the desired image via the ultrasound imaging system. Further, the user will have to correct the parameters associated with that short cut 1006 for the particular view on the system to accommodate for the difference in the current patient anatomy from the standard for all patients. In addition, this correction has to be applied to the parameters associated with each individual short-cut 1006 of the system for all other views to best match the current patient anatomy, and the heart orientation. This is a tedious process and greatly increases the time required for obtaining the desired image dataset for an individual patient.

Further, while the ability to display the 3D and 2D views in conjunction with one another provide enhanced information on the structure being imaged, oftentimes it is difficult, particularly with regard to inexperienced users, to readily identify the anatomical structures being imaged using only the 3D and 2D images presented by the imaging system, such that it is difficult to properly position the probe in order to obtain the optimal 2D view of the structures of interest.

As a result, it is desirable to develop an imaging system and method for improving the visualization of and navigation within the 3D and 2D images provided in an MPR display that can base parameters associated with various short-cuts to particular image views on an anatomical model of the patient anatomy and not a probe location for obtaining the image view.

BRIEF DESCRIPTION OF THE DISCLOSURE

In the present disclosure, 3D and 2D images provided by an ultrasound imaging system from an image dataset utilizing MPR are presented in conjunction with an aligned 3D model of the anatomical structure represented in the images. The system and method provide an automatic, and optionally live, i.e., in motion or in a cine view, aligned and co-oriented display of the 3D anatomical model adjacent to a 3D volume/image and/or one or more 2D MPR views of a 3D echocardiographic dataset. The 3D model is registered to the 3D volume created from the 3D echocardiographic dataset such that the 3D model is aligned with each of the displayed 3D volume and 2D images to provide a visual representation to the user of the orientation of each of the 3D volume and 2D planar views with respect to the 3D model and to one another.

Each 2D planar view is represented in the 3D model to clearly identify the orientation of the 2D planar view relative to the anatomical structure being imaged. In looking at each 2D planar view and the associated 3D model, the user can then immediately and intuitively understand/determine the orientation of the currently displayed data that can be either live or recalled from an associated electronic storage location.

In addition, the 3D model assists the user with regard to the navigation of the 3D dataset using the 3D volume and/or 2D planar views by providing known anatomical reference (s) in the 3D model correlating to the reference(s) in the displayed views. Due to the registration between the 3D model and the 3D volume, the position of a structure of interest in the 3D model can be readily determined and utilized to indicate to the user the navigation and/or positioning of the probe necessary at the proper location in order to obtain the desired 2D view of the structure.

Further, in the system and method employ the anatomical information provided via the detailed anatomical 3D model to generate view bookmarks or short-cuts defined with regard to the 3D anatomical model. These short-cuts utilize the information provided by the anatomical model to determine the optimal positions of 2D images for particular desired MPR views or structures based on the structure of the 3D anatomical model. Because the short-cuts are based on the structure of the 3D model, when the model is registered to a 3D volume generated from the 3D echocardiographic dataset for a patient, the short-cuts are directly applicable to the 3D and 2D cross-sections or MPR images generated from the 3D dataset. Some of those short-cuts are pre-determined by the system, i.e., for factory default views, but the user can also create additional short-cuts based on individual preferences, each of which remain stored in the system with reference to the 3D anatomical model. Further, because these short-cuts are based on the anatomical structure of the 3D model, the short-cuts can be utilized with any 3D volume that is subsequently registered with the 3D model, whether form the same patient or for a different patient altogether.

While interacting with the system to provide the desired 2D MPR views, when the user selects a different short-cut or alternatively interacts with the 3D model to identify a different 2D view for display, the 3D model can shift in accordance with the change in orientation or view desired. As a result of the registration with the 3D model, the system can illustrate the change in 2D views with a morphing motion from the prior short-cut 2D view to the current or selected 2D view. In this manner the system and method provides accurate information to the user on the orientation of the 2D image using the associated 3D model for the various short-cut 2D views.

According to one aspect of the disclosure, an ultrasound imaging system including a probe for obtaining a 3D image dataset on a structure to be imaged, a processor operably connected to the probe and configured to generate a 3D volume and at least one 2D image from the 3D image dataset and a display operably connected to the processor to present the 3D volume and at least one 2D image on the display, wherein the processor is configured to register a 3D anatomical model stored within the ultrasound imaging system to the 3D volume and to display a selected 2D image contained within the 3D volume corresponding to a selected plane within the 3D anatomical model.

According to another aspect of the disclosure, a method for displaying a 2D ultrasound image using an ultrasound imaging system including the steps of obtaining a 3D image dataset with the ultrasound imaging system, generating a 3D volume from the 3D image dataset, registering a 3D anatomical model stored within the ultrasound imaging system to the 3D volume and displaying at least one 2D image contained within the 3D volume corresponding to a selected plane within the 3D anatomical model.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below.

DETAILED DESCRIPTION

The foregoing summary, as well as the following detailed description of certain embodiments of the present invention, will be better understood when read in conjunction with the appended drawings. As used herein, an element or step recited in the singular and proceeded with the word "a" or "an" should he understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

The following description relates to various embodiments of ultrasound imaging. In particular, systems and methods are provided for visualizing intersection information on ultrasound images with the aid of a three-dimensional (3D) model. A three-dimensional (3D) ultrasound dataset may he acquired using an ultrasound imaging system, such as the ultrasound imaging system depicted in FIG. 2, similar to that disclosed in US Patent Application Publication No. US2018/0344290 entitled *Systems And Methods For Displaying intersections On Ultrasound Images,* the entirety of which is expressly incorporated herein by reference for all purposes, and can be used to create a 3D volume and/or one or more 2D planar slices via multi-planar reconstruction (MPR) for presentation on a display for the ultrasound imaging system in association with a 3D model of the anatomical structure being imaged. For example, a graphical user interface, such as the graphical user interfaces depicted in FIGS. 3 and 4 may include a visualization of the 3D model for each MPR 3D/2D image with information displayed thereon regarding the orientation of the image relative to the 3D model, thereby enabling a user to easily navigate the 3D volume.

It should he appreciated that while the various embodiments are described herein with respect to ultrasound imaging, the methods described herein may be implemented with other 3D imaging modalities, including but not limited to computed tomography (CT), magnetic resonance imaging (MRI), positron emission tomography (PET), single photon emission computed tomography (SPECT), and so on.

Figure 2:
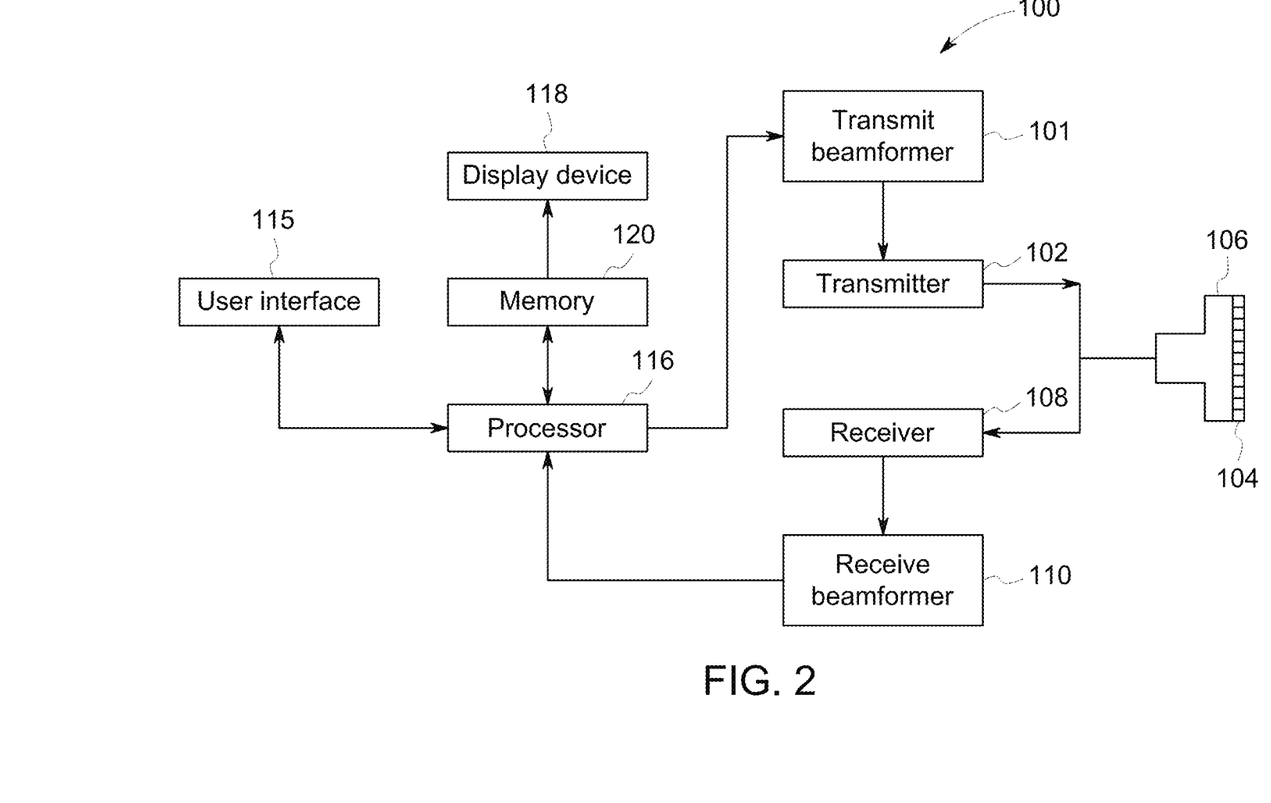
FIG. 2 is a schematic view of an ultrasound imaging system according to an embodiment.

FIG. 2 is a schematic diagram of an ultrasound imaging system 100 in accordance with an embodiment of the invention. The ultrasound imaging system 100 includes a transmit beamformer 101 and a transmitter 102 that drive transducer elements 104 within a probe 106 to emit pulsed ultrasonic signals into a body (not shown). A variety of geometries of probes and transducer elements may be used. The pulsed ultrasonic signals are back-scattered from structures in the body, such as blood cells or muscular time, to produce echoes that return to the elements 104. The echoes are converted into electrical signals, or ultrasound data, by the elements 104 and the electrical signals are received by a receiver 108. The electrical signals representing the received echoes are passed through a receive beamformer 110 that outputs ultrasound data. According to some embodiments, the probe 106 may contain electronic circuitry to do all or part of the transmit anchor the receive beamforming. For example, all or part of the transmit beamformer 101, the transmitter 102, the receiver 108, and the receive beamformer 110 may be situated within the probe 106. The terms "scan" or "scanning" may also be used in this disclosure to refer to acquiring data through the process of transmitting and receiving ultrasonic signals. The term "data" may be used in this disclosure to refer to either one or more datasets acquired with an ultrasound system.

A user interface 115 may be used to control operation of the ultrasound imaging system 100, including controlling the input of patient data, changing a scanning or display parameter, and the like. The user interface 115 may include a graphical user interface configured for display on a display device 118. The graphical user interface may include information to be output to a user (such as ultrasound images, patient data, etc.) and may also include menus or other elements through which a user may enter input to the computing system. In examples described in more detail below with respect to FIGS. 2-4, the user interface may receive inputs from a user indicating, for example, adjustments to the position of planes to be imaged. The user interface 115 may include one or more of the following: a rotary, a mouse, a keyboard, a trackball, a touch-sensitive display, which can also be the display device 118, hard keys linked to specific actions, soft keys that may be configured to control different functions, and a graphical user interface.

The ultras mind imaging system 100 also includes a processor 116 to control the transmit beamformer 101, the transmitter 102, the receiver 108, and the receive beamformer 110. The processor 116 is in electronic communication with the probe 106. For the purposes of this disclosure, the term "electronic communication" may be defined to include both wired and wireless communications. The processor 116 may control the probe 106 to acquire data. The processor 116 controls which of the elements 104 are active and the shape of a beam emitted from the probe 106. The processor 116 is also in electronic communication with a display device 118, and the processor 116 may process the data into images for display on the display device 118. The processor 116 may include a central processor (CPU) according to an embodiment. According to other embodiments, the processor 116 may include other electronic components capable of carrying out processing functions, such as a digital signal processor, a field-programmable gate array (FPGA), or a graphic board. According to other embodiments, the processor 116 may include multiple electronic components capable of carrying out processing functions. For example, the processor 116 may include two or more electronic components selected from a list of electronic components including: a central processor, a digital signal processor, a field-programmable gate array, and a graphic board. According to another embodiment, the processor 116 may also include a complex demodulator (not shown) that demodulates the RF data and generates raw data. In another embodiment, the demodulation can be carried out earlier in the processing chain.

The processor 116 is adapted to perform one or more processing operations according to a plurality of selectable ultrasound modalities on the data. The data may be processed in real-time during a scanning session as the echo signals are received. For the purposes of this disclosure, the term "real-time" is defined to include a procedure that is performed without any intentional delay. For example, an embodiment may acquire images at a real-time rate of 7-20 volumes/sec. The ultrasound imaging system 100 may acquire 2D data of one or more planes at a significantly faster rate. However, it should be understood that the real-time volume-rate may be dependent on the length of time that it takes to acquire each volume of data for display. Accordingly, when acquiring a relatively large volume of data, the real-time volume-rate may be slower. Thus, some embodiments may have real-time volume-rates that are considerably faster than 20 volumes/sec while other embodiments may have real-time volume-rates slower than 7 volumes/sec. The data may be stored temporarily in a buffer (not shown) during a scanning session and processed in less than real-time in a live or off-line operation. Some embodiments of the invention may include multiple processors (not shown) to handle the processing tasks that are handled by processor 116 according to the exemplary embodiment described hereinabove. For example, a first processor may be utilized to demodulate and decimate the RF signal while a second processor may he used to further process the data prior to displaying an image. It should be appreciated that other embodiments may use a different arrangement of processors.

The ultrasound imaging system 100 may continuously acquire data at a volume-rate of, for example, 10 Hz to 30 Hz. Images generated from the display may be refreshed at a similar frame-rate. Other embodiments may acquire and display data at different rates. For example, some embodiments may acquire data at a volume-rate of less than 10 Hz or greater than 30 Hz depending on the size of the volume and the intended application. A memory 120 is included for storing processed volumes of acquired data. In an exemplary embodiment, the memory 120 is of sufficient capacity to store at least several seconds worth of volumes of ultrasound data. The volumes of data are stored in a manner to facilitate retrieval thereof according to its order or time of acquisition. The memory 120 may comprise any known data storage medium.

Optionally, embodiments of the present invention may be implemented utilizing contrast agents. Contrast imaging generates enhanced images of anatomical structures and blood flow in a body when using ultrasound contrast agents including microbubbles. After acquiring data while using a contrast agent, the image analysis includes separating harmonic and linear components, enhancing the harmonic component and generating an ultrasound image by utilizing the enhanced harmonic component. Separation of harmonic components from the received signals is performed using suitable filters. The use of contrast agents for ultrasound imaging is well-known by those skilled in the art and will therefore not be described in further detail.

In various embodiments of the present invention, data may be processed by other or different mode-related modules by the processor 116 (e.g., B-mode, Color Doppler, M-mode, Color M-mode, spectral Doppler, Elastography, TVI, strain, strain rate, and the like) to form 2D or 3D data. For example, one or more modules may generate B-mode, color Doppler, M-mode, color M-mode, spectral Doppler, Elastography, TVI, strain, strain rate, and combinations thereof, and the like. The image beams and/or volumes are stored and timing information indicating a time at which the data was acquired in memory may be recorded. The modules may include, for example, a scan conversion module to perform scan conversion operations to convert the image volumes from beam space coordinates to display space coordinates. A video processor module may be provided that reads the image volumes from a memory and displays an image in real time while a procedure is being carried out on a patient. A video processor module may store the images in the memory as 120, from which the images are read and displayed.

Figure 3:
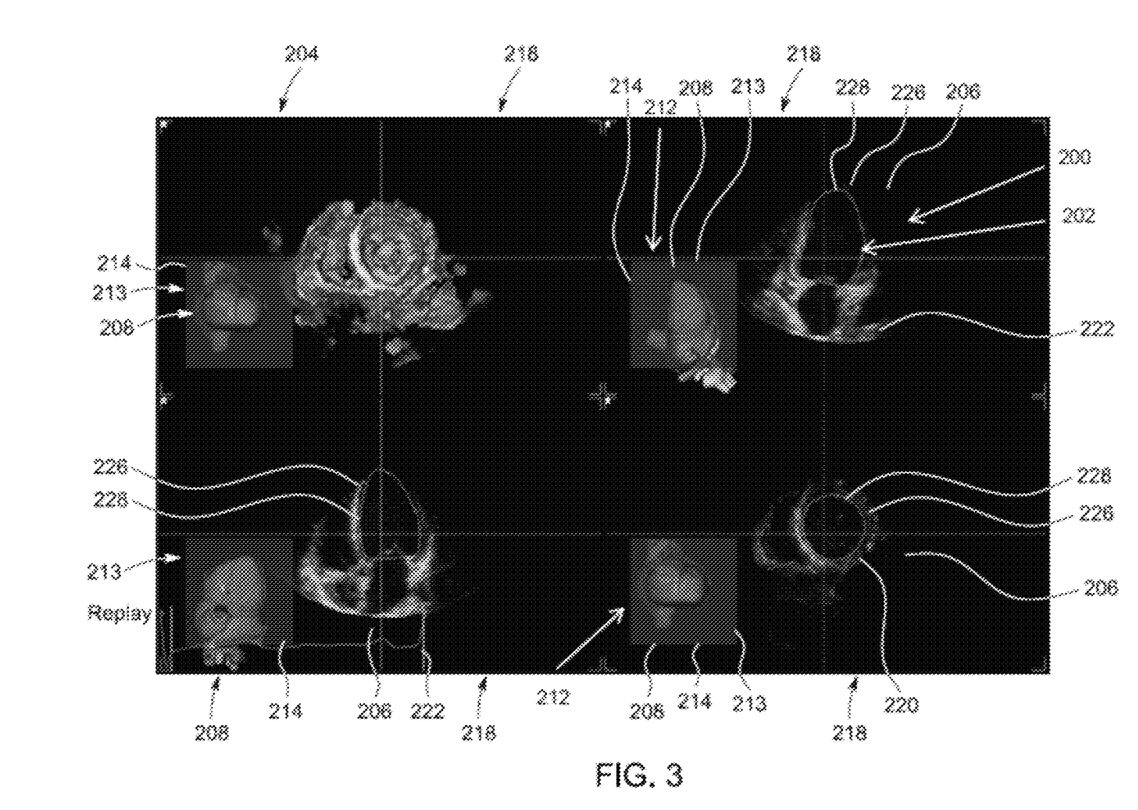
FIG. 3 is an illustration of an exemplary display of multi-planar reconstruction views with an aligned 3D model according to an embodiment.

Referring now to FIG. 3, when the ultrasound imaging system 100 is operated to image an anatomical structure 200 of a patient, such as the heart 202 when obtained in an echocardiographic procedure, the probe 106 obtains a 3D image dataset that is transmitted to the processor 116 for image generation. In doing so, the processor 116 creates a reconstructed 3D volume, image or rendering 204 of the structure 200 from the 3D image dataset. In addition, using the process of multi-planar reconstruction (MPR), the processor 116 generates one or more 2D planar views 206 of predetermined and/or selected slices though the 3D volume/image 204. The 2D planar images 206 are presented on the display 118 in conjunction with the 3D volume/image 204, which in the exemplary embodiment of FIG. 3 shows three (3) 2D planar views 206 in association with the 3D volume/image 204, each disposed in separated windows or frames 218 of the display 118 and identified to indicate the particular view represented by the 2D planar view 206 being displayed, which can be standardized views and/or user-selected views, or combinations thereof.

Along with the creation of the 3D volume/image and 2D planar images 206, the processor 116 has access to a stored 3D anatomical model 208 of the structure being imaged for display in conjunction with the one or more 2D planar views 206 and optionally the 3D volume/image 204. In the method for generation of the 3D anatomical model 208 to be displayed, as best shown in the exemplary embodiment of FIG. 4, in block 300 the processor 116 initially registers a geometrical model 210 that generally represents the form of the imaged structure 200 to the 3D volume/image 204 using known image segmentation methods, such as those disclosed in J. Hansegard, F. Orderud, and S. I. Rabben, "Real-time active shape models for segmentation of 3D cardiac ultrasound," in *Computer Analysis of Images and Patterns*. Berlin, Germany: Springer, 2007, Vol. 4673, LNCS, pp. 157-164, and Orderud et al. U.S. Pat. No. 8,265,363, entitled *Method And Apparatus For Automatically Identifying Image Views In A 3D Dataset*, the entireties of which are each expressly incorporated herein for all purposes, such that the structures and orientation of the geometrical model 210 correspond to those illustrated in the 3D volume/image 204. Subsequently, in block 302 the processor 116 performs a registration between the 3D anatomical model 208 for the imaged structure 200 and the 3D volume/image 204. In this step, the registration is computed by applying a known geometric transformation matrix between the anatomical model 208 and the geometrical model 210 to the transformation matrix resulting from segmentation in order to correlate the structure of the anatomical model 208 to the structures of the 3D volume/image 204, such that the orientation, structure(s) and point(s) of the 3D anatomical model 208 are known and correspond in the 3D coordinate system to those present in the 3D volume/image 204. Once the 3D anatomical model 208 is registered to the 3D volume/image 204, in block 304 the 3D model 208 can be oriented and displayed in association with the 3D volume/image 204 and each 2D planar view/image 206 with the orientation of each 3D model 208 corresponding to the orientation of the particular image 204,206 associated with the individual 3D model 208.

With regard to the registration of the 3D anatomical model 208 to the 3D volume/image 204, in an alternative embodiment the 3D anatomical model 208 can also be a deformable 3D anatomical model 208. In this embodiment, the 3D image dataset used to form the 3D volume/image 204 can be applied to the 3D anatomical model 208 and/or the geometrical model 210, in order to deform or warp the structure of the 3D anatomical model 208 and/or geometrical model 210 to conform more specifically to the actual form of the anatomical structure 200 of the patient being imaged.

Figure 4:
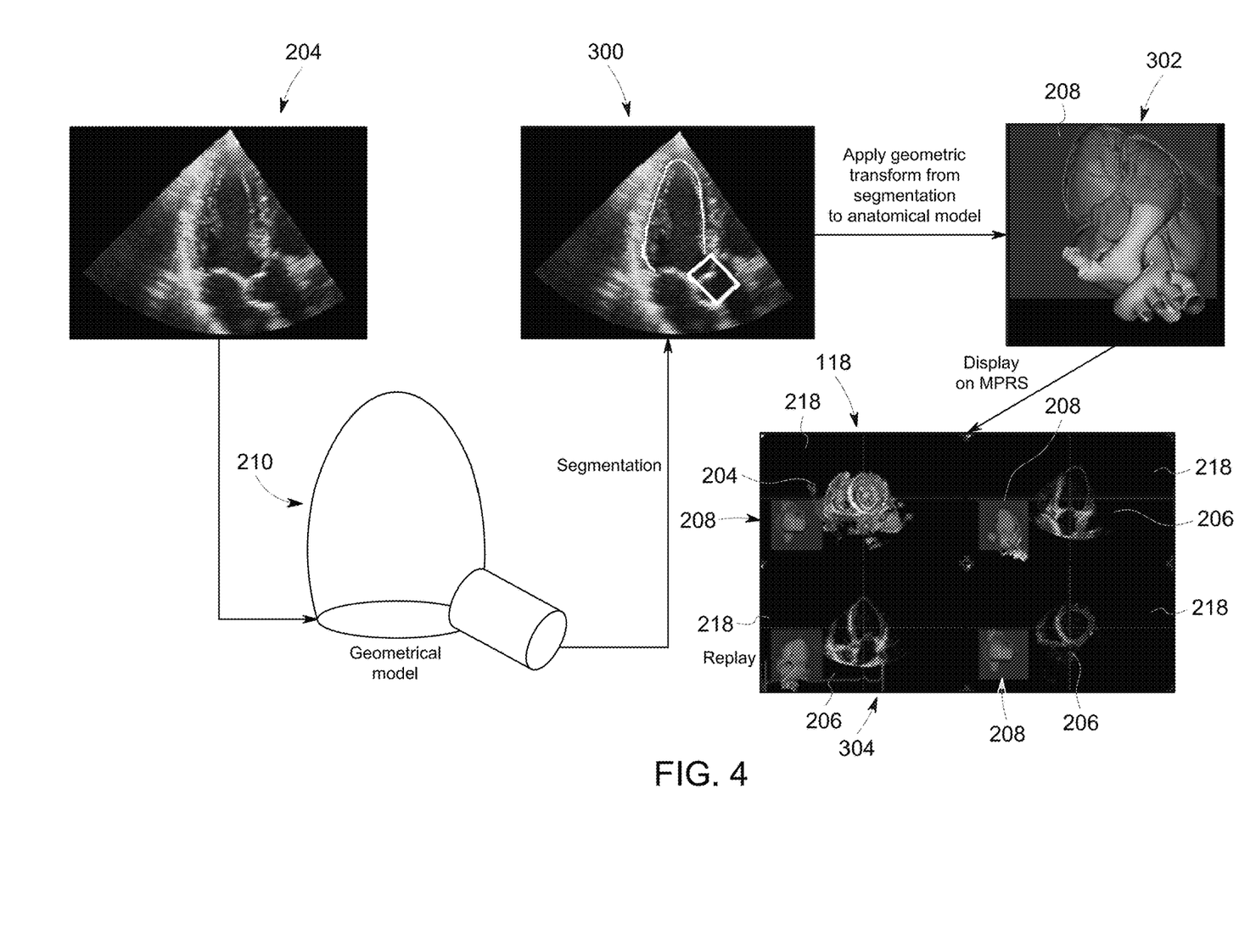
FIG. 4 is an illustration of a method of the registration and alignment of a 3D model with multi-planar reconstruction views according to an embodiment.

After the registration and optional deformation of the 3D anatomical model 208 to the 3D volume/image 204, the model 208 can be presented on the display 118 in conjunction with one or more of the 3D volume/image 204 and the 2D planar MPR images 206, as shown in FIGS. 3-4.

With regard to the manner of the presentation of the model 208 on the display 118, in the illustrated exemplary embodiment of FIG. 3, the model 208 is presented within one of a number of frames 218 on the display 118 in association with each of the 3D volume/image 204 and the number of 2D planar images 206 on the display 118, optionally in a scale suitable to show the structure of the model 208 without detracting from the information provided by each of the images 204,206. However, in alternative embodiments the model 208 can be displayed with any combination of the images 204,206, such as with only each of the one or more 2D planar images 206 presented on the display 118. Each of the 2D planar images 206 is associated with a particular default, standardized and/or selected view, or combinations thereof, through the imaged structure 200 in order to provide information about the condition of the imaged structure 200. As the 3D model 208 is registered in the 3D coordinate space with the image 204,206, the presentation of the 3D model 208 for each image is oriented to the plane 212 being viewed in/displayed by the 3D volume/image 204 or containing the 2D planar view 206. As such, the plane 212 of each respective image 204,206 presented on the display 118 is identified within the associated 3D model 208 by an icon 213 of any suitable shape and/or color, such as a shaded square 214 aligned with the plane 212 of each image 204,206. To align the square 214 with the associated image plane 212, the 3D model 208 is rotated/oriented to place the square 214 within the plane of the display 118 on which the images 204,206 are presented. In this manner, on the display 118 the user is presented with the various images 204,206 and the model 208 showing the plane 212 for the specific image 204,206 (as represented by the square 214 within the model 208) and the orientation of the image 204,206 with respect to the model 208, which significantly assists in the understanding of the location of the 2D planar images 206 on the structure 200, and any required navigation to a desired region of interest within the imaged structure 200.

In another exemplary embodiment, the display 118 presents a 2D planar view 206 that is obtained in a live manner by a user positioning the probe 106 on the patient, and a separate view of the 3D model 208, which may optionally also be presented on the display 118 or can solely be utilized as an internal reference by the system 100/processor 116.

In an embodiment where the live registered 3D model 208 is presented on the display 118 during acquisition in conjunction with the 2D view 206, the 3D model 208 provides the user an understanding of the currently scanned anatomy illustrated in the 2D view 206 relative to the 3D model 208. This can provide useful information during scanning in 3D or 4D, especially for inexperienced users, since by looking at the 3D model 208, and the associated 2D image 206 the user can orient the probe 106 in order to achieve optimal acquisition for the desired 2D image 206. In addition, apart from movement of the probe 106 by the user to alter the 2D view 206, the user can interact directly with the 3D model 208 (or the 2D image 206) to alter and/or determine the 2D image 206 being displayed, e.g., the user can employ the user interface 115 to click at the 3D model 208 on the display 118 such as to enlarge the model 208 and 2D image 206, to rotate the 3D model 208 and the 2D image 206, and to draw slices on the 3D model 208 to identify the 2D planar view 206 to be displayed.

The view of the 3D model 208 additionally includes a plane or slice 214 represented in the model 208 that, as result of the registration between the 3D volume 204 and the 3D model 208 described previously, corresponds to the plane of the 2D image 206 presented in conjunction with the 3D model 208. In the 3D anatomical model 208 the location of all features of interest and views of interest are known. Consequently, due to the registration of the 3D volume image 204 with the 3D model 208 during live acquisition of the 3D volume/image 204 or when analyzing a recorded 3D volume/image 204, the location and/or orientation of these features of interest and views of interest are also known in the 3D volume/image 204, as well as optionally the position of the probe 106 based on the correspondence of the image data/imaging field from the probe 106 with the registered 3D volume 204 and 3D model 208. Further, by interacting with the 3D model 208, the user can change the orientation of the 3D model 208 to any desired view, such as shown in FIG. 3, with the plane 214 being represented in an orientation corresponding to the location of the plane 214 in the selected orientation for the 3D model 208.

Figure 5:
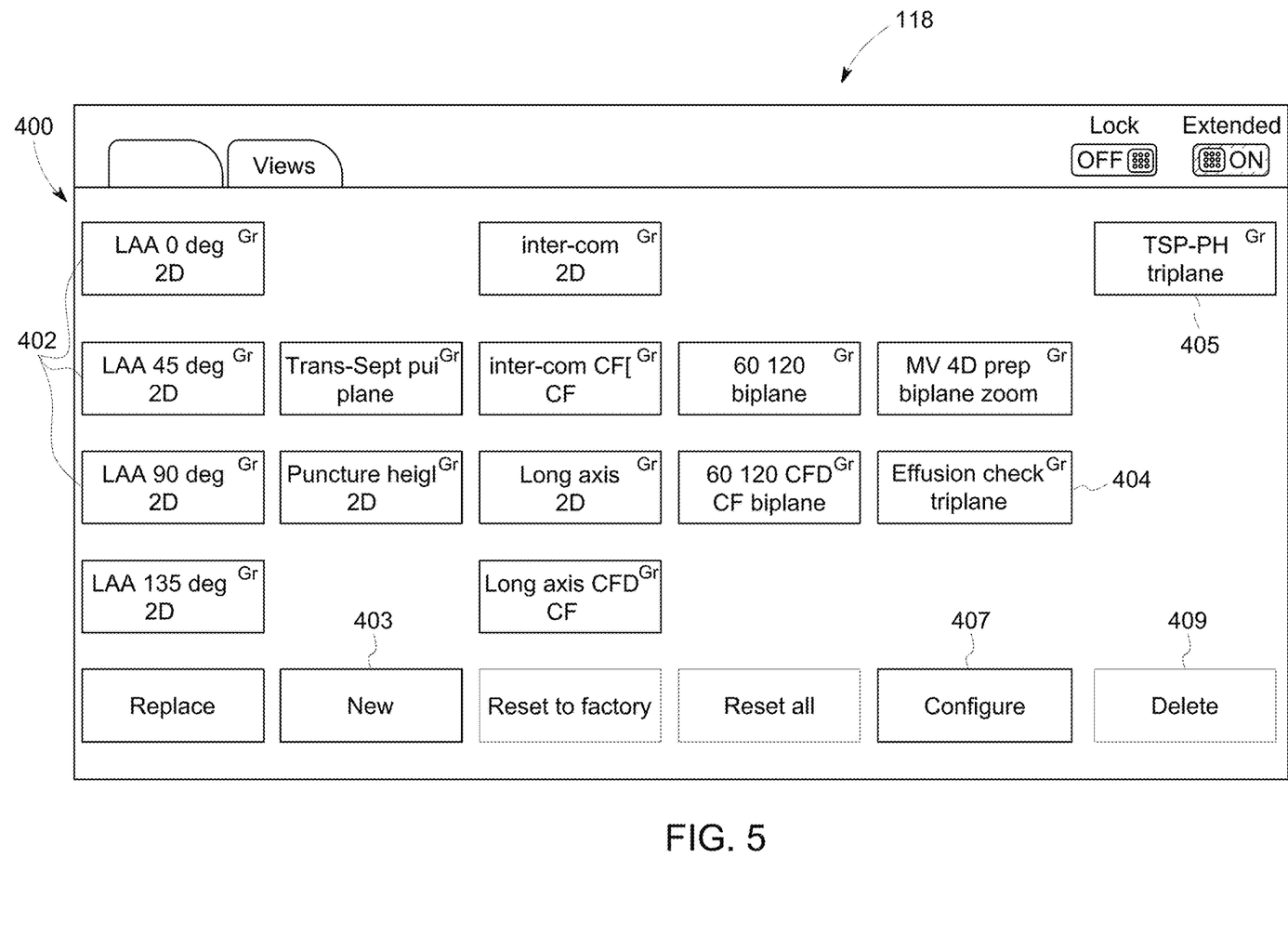
FIG. 5 is an illustration of an exemplary display screen including short-cut selections associated with various standard and user-defined 2D views according to an embodiment.

As such, in one exemplary embodiment as shown in FIG. 5, the user can select from a list or array 400 of short-cuts 402 stored within memory 120 and provided to the user by the system 100 in a suitable manner to navigate to a particular view of interest/2D planar view 206 of the 3D volume 204. The bookmarks or short-cuts 402 each correspond to a standard or user-defined 2D view of the imaged structure 200 that is used in the evaluation and/or diagnosis of any conditions present in the structure 200. The short cuts 402 are associated with 2D planes 212 within the 3D model 208 having imaging parameters for the 2D planes 212, such as the depth, gain, angle, and 2D plane 212 position and orientation in the 3D volume 208, for example, stored in memory 120 in association with the shortcut 402. All of the imaging parameters for the 2D plane 212 associated with the short cut 402 to the selected 2D view 206 are determined in relation to the 3D model 208, and not with the regard to the position of the probe 106 relative to the patient, as in the prior art. Therefore, when a particular short-cut 402 is selected by the user, the 2D image 206 displayed from the 3D volume 204 is associated with the imaging parameters for the 2D plane 212 relative to the structure of the 3D model 208 registered to the 3D volume 204.

Regardless of whether the 3D volume 204 registered to the 3D model 208 is acquired live or from an electronic storage device or database, e.g., memory 120, operably connected to the system 100, the processor 116 can readily display the orientation of the 2D view(s) 206 associated with the selected short-cut 402 by accessing the image parameters in memory 120 for the selected short-cut 402/2D view 206 and illustrating a slice 214 on the 3D model 208 corresponding to the location of the selected 2D view 206 on the 3D model 208. If the 2D image/view 206 is obtained from a stored 3D volume 204, the processor 116 can simply present the selected 2D view 206 along the slice (not shown) of the 3D volume 204 corresponding/registered to the slice 214 of the 3D model 208.

Figure 6:
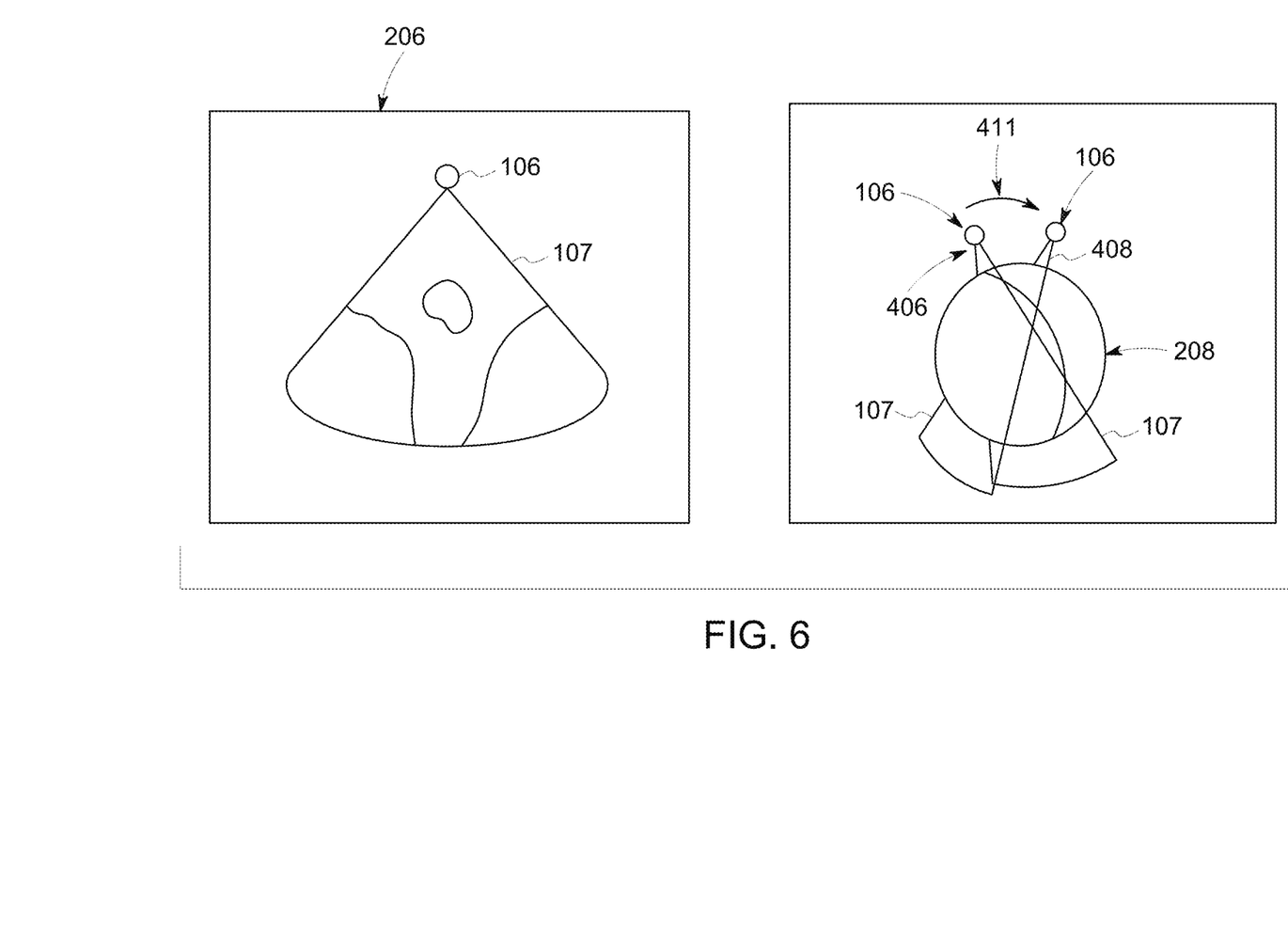
FIG. 6 is a schematic view of an exemplary display illustrating a 2D planar view and a 3D model having a representation of a current 2D view and a selected 2D view in the 3D model according to an embodiment.

If a 2D image/view 206 is being obtained live, the processor 116 can present the 2D view 206 along the slice (not shown) of the 3D volume 204 corresponding/registered to the slice 214 of the 3D model 208 as done for the stored 3D volume 204. Alternatively, as shown in FIG. 6, the system 100/processor 116 or can provide an indication to the user of the proper location for the probe 106 in order to obtain the desired 2D image/view 206 represented by the slice 214. To provide this indication, using the registration of the live 3D volume 204 to the 3D model 208, the processor 116 can use any suitable navigation instruction, such as by providing an optional indication 406 on the 3D model 208 of the actual or current position/imaging plane of the probe 106, and a separate indication 408 of the required or selected position/imaging plane of the probe 106 to obtain the selected 2D image 206 along with an optional navigation icon 411, e.g., arrows, showing the direction of movement for the probe 106 required to move to the required position of the probe 106 for the selected 2D image 206. In this manner, the processor 116 can direct or navigate the user to the proper location for the probe 106 to match that required for the slice 214 corresponding to the desired 2D view represented by the short-cut 402.

For example, the "perfect" 3-chamber view can be well defined in the 3D anatomical model 208. After registration of the live or stored 3D volume/image 204 to the 3D model 208, the user can select the short-cut 402 associated with the 3-chamber view and processor 116 can present the 2D image 206 associated with the image or view parameters for the 3-chamber view on the 3D model 208, but applied to the 3D volume/image 204 based on the registration and/or present the location for the probe 106 that the user needs to move the probe 106 to provide the desired 3-chamber view. Further, since in live acquisitions of the 3D dataset for the 3D volume/image 204, the reconstructed 3D volume/image 204 and the 3D model 208 are continuously and automatically registered in the background by the processor 116, the user can access to any of the views of interest using the short-cuts 402 to provide navigation directions for the position of the probe 106 for any selected short-cut 402 during the live acquisition procedure. Also, as the user moves/rotates the probe 106 and correspondingly the 2D image/view 206 presented on the display 118 when acquiring live image data, the 3D model 208 will move/rotate in lockstep with the movement of the displayed 2D image 206.

According to another exemplary embodiment, referring again to FIG. 5, apart from the pre-determined or standard 2D planar views 206 provided by the system 100, the user can create new short-cuts 404 relating to views that are defined using the 3D model 208 but for images that are selected by the user. For example, in an interventional procedure where certain 2D views 206 are desired from a 3D volume/image 204 obtained in the procedure in addition to the standard 2D views 206 provided by the short-cuts 402, the user can place the probe 106 in a location corresponding to the desired 2D view 206. The system 100 then enables the user to define a new (short-cut add function 403) specific short-cut 404 corresponding to the location of the 2D image/view 206 in the 3D model 208 based on the registration between the 3D model 208 and the 3D volume 204. This short-cut 404, and the corresponding imaging parameters relative to the 3D model 208 for the 2D view 206 associated with the short-cut 404, is stored by the system 100 in memory 120 in addition to the parameters for the standard short-cuts 402. Because the parameters for the user-selected 2D view 206 represented by the short-cut 404 are relative to the 3D model 208 stored in the memory 120 of the system 100, the short-cut 404 can also be used to obtain the same 2D view 206 in other 3D volumes 204 from other patients that have been registered to the 3D model 208 stored in the memory 120 of the system 100. Further, each of the user-defined short-cuts 404 can be deleted from the memory 120 (short-cut delete function 409) and from the 3D model 208 and/or re-configured or edited (short-cut edit function 407) in the 3D model 208 stored in memory 120 on the system 100 by the user. Also, the user-defined short-cuts 404 can be grouped together in a single short-cut 405, such as for a number of desired 2D views 206 associated with a particular interventional and/or diagnostic procedure. Then, when a user loads a new 3D volume 204 from storage or in a live acquisition to the system 100, the user can automatically acquire all the 2D images 206 associated with the short-cut 405 in the 3D model 208 once the anatomical model 208 is automatically registered with the 3D volume 204. The user does this by selecting the group short-cut 405 to enable the processor 116 to access the image parameters for each 2D image 206 in the 3D model 208 stored in memory 120 in association with the group short-cut 405, and to subsequently display each 2D image 206 in the registered 3D volume 204 corresponding to the stored locations/imaging parameters for the group short-cut 405.

Figure 7:
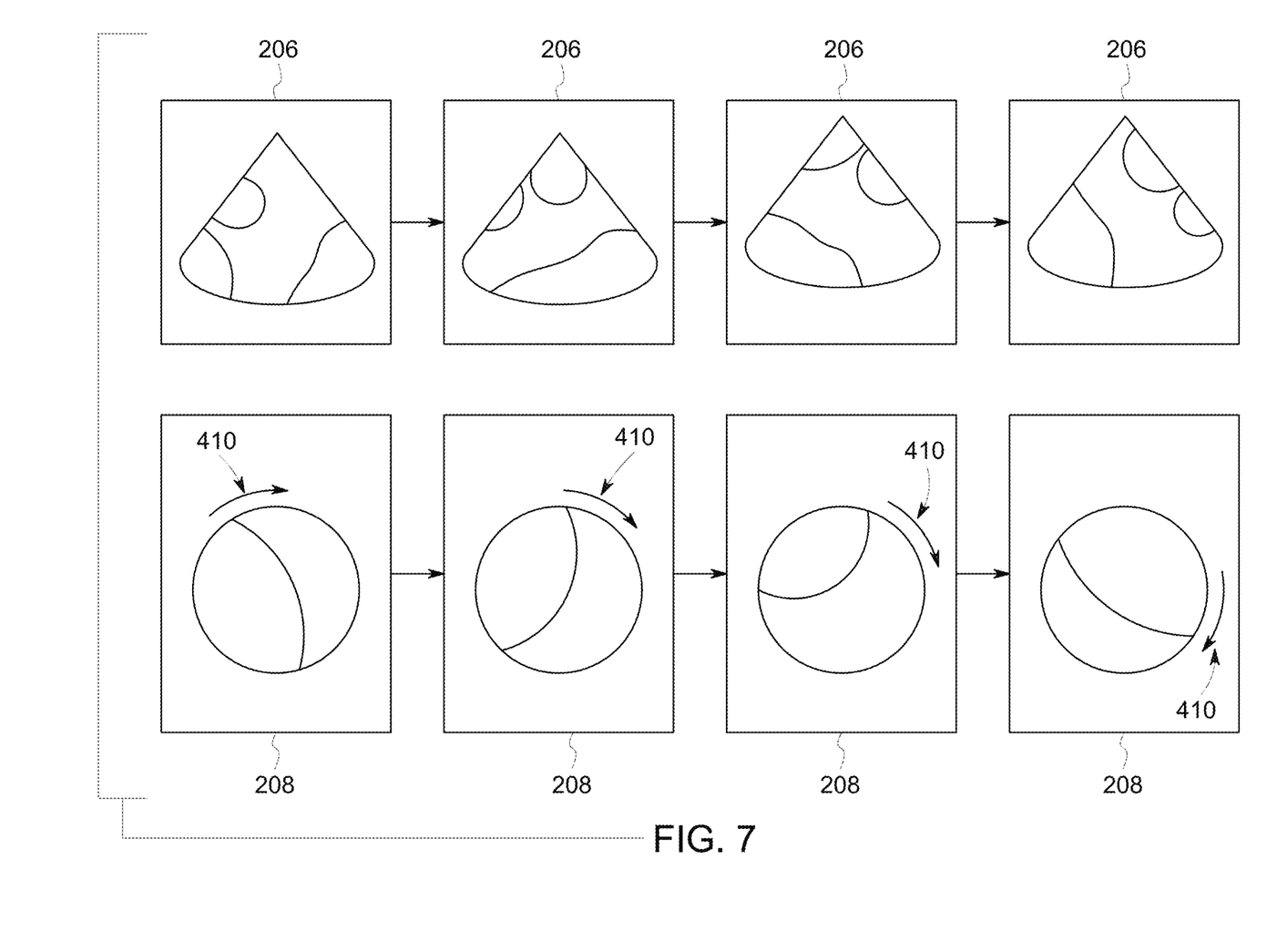
FIG. 7 is an illustration of the morphing motion of a 2D view and 3D model when switching between selected 2D views according to an embodiment.

Looking now at the exemplary embodiment of FIG. 7, as a further benefit of the correlation of the stored image parameters for the short-cuts 402,404 with the anatomical structure of the 3D model 208, the exact positions of the 2D views 206 for each short-cut 402,404 relative to one another are also known. Therefore, when a user transitions between the different 2D views 206 associated with different short-cuts 402,404, such as when the user selects a series of short-cuts 402,404 to display the associated 2D images 206, the 2D image 206 currently being displayed can be presented with a slow motion, or "morphing" movement of the displayed image. In this morphing movement shown on the display 118, there is an animated transition on the display 118 from the location and orientation for the current 2D image 206 to the location and orientation of the selected 2D image 206. The movement or transition of the 2D image 206 through one or more intervening 2D images 206 located or disposed between the current 2D image 206 and the selected 2D image 206 assists a user to understand the spatial and anatomical relationship between the two 2D views 206. This morphing movement of the displayed 2D image 206 can optionally be shown in conjunction with an illustration of this motion, e.g., arrows 410, on the 3D anatomical model 208 illustrating the direction of the movement on the 3D model 208 between the 2D views 206, or rotation of the 3D model 208, or of the plane 214 in the 3D model 208 illustrating the location of the plane of displayed 2D image 206, or combinations thereof.

Figure 8:
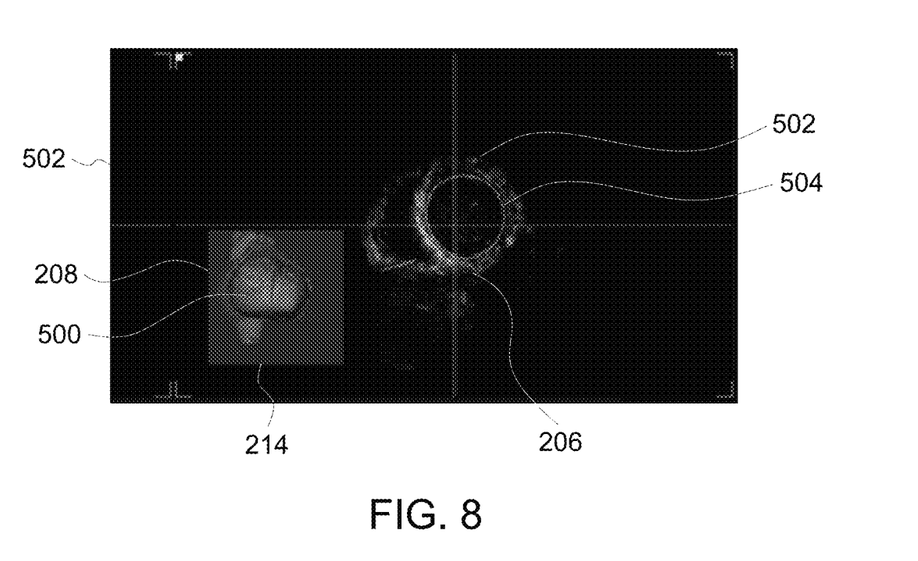
FIG. 8 is a schematic view of an exemplary display including anatomical orientation information in the 2D view and the 3D model.

Referring now to the exemplary embodiment illustrated in FIG. 8, with the readily known structure of the stored 3D anatomical model 208, any structure or feature of interest 500, e.g., the left atrial appendage, the mitral valve center, the right ventricle, etc., and any direction of interest 502, e.g., patient left, patient right, anterior, posterior, etc., can be easily defined in the 3D model 208 and illustrated in the 3D volume 204 and/or 2D planar image 206 using the registration between the 3D model 208 and the 3D volume 204. After the 3D anatomical model 208 has been registered to the patient 3D volume/image 204, the feature of interest 500 and direction of interest 502 can be displayed in the 3D model 208 together with the 3D volume 204/and/or 2D planar image 206 providing the user anatomical orientation for the acquired images 204,206. The feature(s) 500 and direction(s) 502 can be displayed in the form of highlighting, such as by providing an outline 504 in the image 204,206 representing the location of the selected feature 500 and/or direction 502. Alternatively, or in combination with the outline 504, the labeling can be performed in one or more of the model 208 and/or images 204, 206 using color coding (not shown), e.g., illustrating the left ventricle in red, right ventricle in blue, etc., as readable text and/or automatic labeling (not shown) located within the associated 2D planar images 206, and/or as arrows in the space around the images 204,206 indicating the directions 502, e.g., patient left, patient right, etc.

In alternative embodiments, when the 3D dataset is acquired in real-time, such that the 3D volume 204 and the one or more 2D planar images 206 can be presented in motion, e.g., in a cine view, the registration of the 3D model 208 to the 3D volume 204 can enable the 3D model 208 to be presented in motion as a 4D model 208 along with the 3D volume 204 (4D volume 204) and 2D planar views images 206 (3D planar images). The motion of the 3D model 208 can be determined as one or more averages of the position(s) of different structures in the 3D volume 204 and/or averages of the motion of those structures.

The written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A method for displaying a 2D multi-planar reconstruction ultrasound image using an ultrasound imaging system, the method comprising the steps of:
   obtaining a 3D image dataset with the ultrasound imaging system;
   generating a 3D volume from the 3D image dataset;
   registering a 3D anatomical model stored within the ultrasound imaging system to the 3D volume;
   displaying a 2D multi-planar reconstruction image contained within the 3D volume corresponding to a selected plane within the 3D anatomical model; and
   identifying the selected plane in the 3D anatomical model, wherein the step of identifying the selected plane comprises selecting a short cut on the ultrasound imaging system displayed separate from the 3D anatomical model and associated with the selected plane in the 3D anatomical model,
   wherein the method further comprises the step of defining the short cut by storing imaging parameters for a user-defined 2D plane in the 3D anatomical model in association with the short cut.

2. The method of claim 1, wherein the step of defining the short cut comprises:
positioning an imaging probe at a location to obtain the multi-planar reconstruction 2D image within the 3D volume; and
storing imaging parameters within the memory for the multi-planar reconstruction 2D image relating to the position of the multi-planar reconstruction 2D image relative to the 3D model.

3. The method of claim 2, wherein the step of registering the 3D anatomical model to the 3D volume comprises:
registering a geometrical model to the 3D volume; and
registering the geometrical model to the 3D anatomical model.

4. The method of claim 2, wherein the imaging parameters include probe image depth, probe image gain, probe angle, position and orientation of 2D multi-planar reconstruction image within the 3D volume and combinations thereof.

5. The method of claim 2, wherein the step of identifying the selected plane in the 3D anatomical model further comprises:
displaying the 3D anatomical model; and
illustrating the selected plane in the 3D anatomical model corresponding to the 2D multi-planar reconstruction image.

6. The method of claim 5, wherein the step of illustrating the plane in the 3D anatomical model comprises:
illustrating a first plane corresponding to a location of a first 2D multi-planar reconstruction image defined by current location of a probe operably connected to the ultrasound imaging system; and
illustrating a second plane corresponding to a location of a second 2D multi-planar reconstruction image defined by the short cut on the ultrasound imaging system associated with the selected plane in the 3D anatomical model.

7. The method of claim 6, further comprising the step of illustrating a navigation icon between the first plane and the second plane.

8. A method for displaying a 2D multi-planar reconstruction ultrasound image using an ultrasound imaging system, the method comprising the steps of:
obtaining a 3D image dataset with the ultrasound imaging system;
generating a 3D volume from the 3D image dataset;
registering a 3D anatomical model stored within the ultrasound imaging system to the 3D volume; and
displaying a 2D multi-planar reconstruction image contained within the 3D volume corresponding to a selected plane within the 3D anatomical model,
wherein the step of displaying the 2D multi-planar reconstruction image contained within the 3D volume corresponding to a selected plane within the 3D anatomical model comprises:
displaying a first 2D multi-planar reconstruction image within the 3D volume corresponding to a first selected plane within the 3D anatomical model;
selecting a second 2D multi-planar reconstruction image within the 3D volume corresponding to a second plane within the 3D anatomical model; and
morphing the first 2D multi-planar reconstruction image through the 3D volume to the second multi-planar reconstruction 2D image.

9. The method of claim 8, further comprising providing an illustration of the movement from the first 2D multi-planar reconstruction image to the second 2D multi-planar reconstruction image on the 3D anatomical model.

10. The method of claim 9, wherein the step of providing the illustration of the movement from the first 2D multi-planar reconstruction image to the second 2D multi-planar reconstruction image comprises providing an arrow on the 3D anatomical model in the direction of the 2D multi-planar reconstruction image movement.

11. The method of claim 10, wherein the step of providing the illustration of the movement from the first 2D multi-planar reconstruction image to the second 2D multi-planar reconstruction image comprises rotating the 3D anatomical model.

12. An ultrasound imaging system comprising:
a probe for obtaining a 3D image dataset on a structure to be imaged;
a processor operably connected to the probe and configured to generate a 3D volume and one or more 2D multi-planar reconstruction images from the 3D image dataset;
a memory operably connected to the processor and containing information on a 3D anatomical model and imaging parameters for one or more selected 2D planes within the 3D anatomical model; and
a display operably connected to the processor to present the 3D volume and the one or more 2D multi-planar reconstruction images on the display,
wherein the processor is configured to register the 3D anatomical model to the 3D volume and to display a selected 2D multi-planar reconstruction image contained within the 3D volume corresponding to the image parameters for the selected 2D plane within the 3D anatomical model,
wherein the processor is configured to display an array of short cuts separate from the 3D anatomical model, each of the array of short cuts stored in the memory and including pre-defined imaging parameters for standard and user-defined views-associated with one selected 2D plane in the 3D anatomical model, to receive an indication of a selection of a short cut, and to display the 2D multi-planar reconstruction image contained within the 3D volume corresponding to the image parameters of the selected 2D plane for the selected short cut, and
wherein the processor is configured to receive imaging parameters for a user-defined 2D multi-planar reconstruction image within the 3D volume, and to store in the memory the imaging parameters for the selected 2D plane in the 3D model corresponding to the user-defined 2D multi-planar reconstruction image as a user-defined short cut.

13. An ultrasound imaging system comprising:
a probe for obtaining a 3D image dataset on a structure to be imaged;
a processor operably connected to the probe and configured to generate a 3D volume and one or more 2D multi-planar reconstruction images from the 3D image dataset;
a memory operably connected to the processor and containing information on a 3D anatomical model and imaging parameters for one or more selected 2D planes within the 3D anatomical model; and
a display operably connected to the processor to present the 3D volume and the one or more 2D multi-planar reconstruction images on the display,
wherein the processor is configured to register the 3D anatomical model to the 3D volume and to display a selected 2D multi-planar reconstruction image contained within the 3D volume corresponding to the image parameters for the selected 2D plane within the 3D anatomical model, and wherein the processor is configured to display a first 2D multi-planar reconstruction image within the 3D volume corresponding to a first selected 2D plane within the 3D anatomical model, to determine the location of a second 2D multi-planar reconstruction image within the 3D volume corresponding to a second selected 2D plane within the 3D anatomical model, and to morph the first 2D multi-planar reconstruction image through the 3D volume to the second multi-planar reconstruction 2D image.

14. The system of claim 13, wherein the processor is configured to display an illustration of the movement from the first 2D multi-planar reconstruction image to the second 2D multi-planar reconstruction image on the 3D anatomical model.

15. The system of claim 12, wherein the processor is configured to identify a feature of interest in the 3D anatomical model, and to display a selected 2D multi-planar reconstruction image contained within the 3D volume corresponding to the image parameters for the selected 2D plane within the 3D anatomical model with an indication of the feature of interest in the selected 2D multi-planar reconstruction image.

* * * * *